United States Patent [19]

Chu

[11] Patent Number: 4,542,133
[45] Date of Patent: Sep. 17, 1985

[54] METHYLENEDIOXY QUINO-BENOXAZINE DERIVATIVES AND ANTIBACTERIAL USE

[75] Inventor: Daniel T. Chu, Vernon Hills, Ill.

[73] Assignee: Abbott Laboratories, North Chicago, Ill.

[21] Appl. No.: 604,191

[22] Filed: Apr. 26, 1984

[51] Int. Cl.$^4$ .................... A61K 31/535; C07D 498/14
[52] U.S. Cl. .................... 514/232; 514/233; 514/236; 544/99
[58] Field of Search .................... 544/99; 424/248.52, 424/248.53, 248.55

[56] References Cited

U.S. PATENT DOCUMENTS

| | | | |
|---|---|---|---|
| 4,017,622 | 4/1977 | Minami et al. | 424/250 |
| 4,292,317 | 9/1981 | Pesson | 424/250 |
| 4,382,892 | 5/1983 | Hayakawa et al. | 544/101 X |
| 4,439,436 | 3/1984 | Wentland et al. | 424/258 |
| 4,443,447 | 4/1984 | Gerster et al. | 544/101 X |
| 4,473,568 | 9/1984 | Hutt | 544/101 X |

FOREIGN PATENT DOCUMENTS

| | | |
|---|---|---|
| 78362 | 5/1983 | European Pat. Off. |
| 1147336 | 4/1969 | United Kingdom |

OTHER PUBLICATIONS

SCHM 84-063204/11 (1984) DD 204,089-A.
DAUC 84-039639/07 (1984) J5 9001,489-A.
DAUC 84-043150/08 (1984) EP 101,829-A.

*Primary Examiner*—Richard L. Raymond
*Attorney, Agent, or Firm*—Steven F. Weinstock; Martin L. Katz

[57] ABSTRACT

1,2-methylenedioxy quino-benoxazine derivatives having the formula:

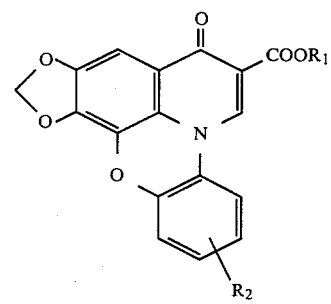

wherein $R_2$ is a substituent and $R_1$ is hydrogen or a carboxy protecting group. The compounds of the invention have antibacterial activity.

9 Claims, No Drawings

METHYLENEDIOXY QUINO-BENOXAZINE DERIVATIVES AND ANTIBACTERIAL USE

This invention relates to new quino-benoxazine derivatives having antibacterial properties, compositions containing the new quino-benoxazine derivatives and methods of treating mammalian patients with the new quino-benoxazine derivatives.

It is known that certain quinoline compounds exhibit antibacterial properties, notably certain 7-piperazinyl-4-oxo-1,4-dihydroquinoline-3-carboxylic acids. In U.S. Pat. No. 4,017,622 there are disclosed certain 7-piperazinyl-4-oxo-1,4-dihydroquinoline-3-carboxylic acid derivatives which are substituted in the 1-position with an alkyl, benzyl or acetyl substituent. U.S. Pat. No. 4,292,317 discloses derivatives of 7-piperazinyl-4-oxo-4-dihydroquinoline-3-carboxylic acids wherein the 1-position is substituted by an alkyl group or a vinyl group. In U.S. Pat. No. 4,284,629 there are disclosed various 4-oxo-1,4-dihydroquinoline-3-carboxylic acids in which the 1-position is substituted with a cycloalkyl group.

This invention relates to novel antibacterial agents and, more particularly, to 1,2-methylenedioxy-4-oxo-4H-quino[2,3,4-i,j][1,4]benoxazine-5-carboxylic acids and derivatives having the formula:

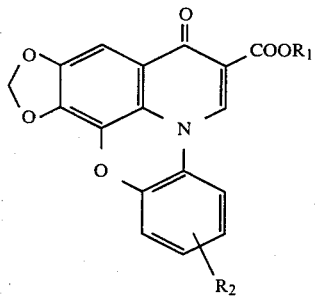

(I)

wherein $R_2$ is one or more of hydrogen, halogen, $C_1$ to $C_6$ alkyl including substituted derivatives thereof, carboxyl, cyano, methylenedioxy, a group having the formula —Y—$R_3$ wherein —Y— is —O— or —S—; and $R_3$ is hydrogen or $C_1$ to $C_6$ alkyl and an amine having the formula:

wherein $R_4$ and $R_5$ are each independently hydrogen or $C_1$ to $C_6$ alkyl.

$R_1$ is hydrogen or a carboxy-protecting group.

As used herein, the term "halogen" refers to chloro, bromo, fluoro and iodo groups, while the term "$C_1$ to $C_6$ alkyl" refers to loweralkyl groups including methyl, ethyl, propyl, isopropyl and butyl.

As indicated above, $R_2$ can be $C_1$ to $C_6$ alkyl as well as hydroxy and halo-substituted derivatives thereof. Such groups include a chloromethyl group, a chloroethyl group, a chloropropyl group, a hydroxyethyl group, and a trifluoromethyl group.

$R_2$ can also be a group of the formula —Y—$R_3$. Representative groups of this type include a hydroxy group, a mercapto group, a lower alkoxy group, such as methoxy, ethoxy, propoxy, as well as the thio analogs thereof, namely a methylmercapto group, and an ethylmercapto group.

As used herein, the term "carboxy-protecting group" refers to and includes the residue of a carboxylic acid ester group. Such carboxy-protecting groups are well known to those skilled in the art, having been extensively used in the propection of carboxyl groups in the penicillin and cephalosporin fields, as described in U.S. Pat. Nos. 3,840,556 and 3,719,667, the disclosures of which are incorporated herein by reference. In general, such carboxy-protecting groups can be relatively easily cleaved to yield the corresponding free carboxy group. Representative protecting groups include $C_1$–$C_8$ alkyl (e.g., methyl, ethyl, tertiary butyl), substituted alkyl (e.g., dimethylaminoethyl), benzyl and substituted derivatives thereof such as alkoxy and nitrobenzyl groups; also suitable are acyl groups such as pivaloyloxymethyl groups.

The preferred compounds of the present invention are those having the structure:

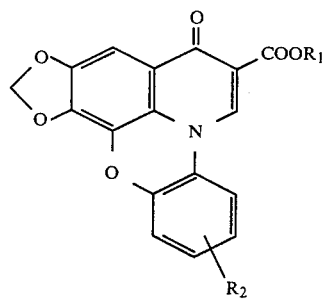

wherein $R_1$ is as described above and $R_2$ is one or more of alkyl or halogen.

Representative of such preferred compounds are 1,2-methylenedioxy-4-oxo-4H-quino[2,3,4-i,j][1,4]benozazine-5-carboxylic acid, 1,2-methylenedioxy-10-fluoro-4-oxo-4H-quino[2,3,4-i,j][1,4]benoxazine-5-carboxylic acid, 1,2-methylenedioxy-8,10-difluoro-4-oxo-4H-quino[2,3,4-i,j][1,4]benoxazine-5-carboxylic acid, 1,2,9,10-dimethylenedioxy-4-oxo-4H-quino[2,3,4-i,j][1,4]benoxazine-5-carboxylic acid, 1,2-methylenedioxy-10-methyl-4-oxo-4H-quino[2,3,4-i,j][1,4]benoxazine-5-carboxylic acid.

Also included within the scope of the present invention are pharmaceutically acceptable salts of the foregoing compounds. As used herein, the term "pharmaceutically acceptable salts" refers to nontoxic acid addition salts and alkaline earth metal salts of the compounds of Formula I. The salts can be prepared in situ during the final isolation and purification of the compounds of formula I, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali or alkaline earth metal salts include the sodium, calcium, potassium and magnesium salts. It has been found that the compounds of the present invention possess antibacterial activity against a wide spectrum of gram positive and gram negative bacteria, as well as enterobacteria. The compounds of the invention are therefore useful in the antibiotic treatment of susceptible bacterial infections in both humans and animals. In addition, the compounds, by reason of their in vitro activity, may be used in scrub solutions for surface inhibition of bacterial growth.

Susceptible organisms generally include those gram positive and gram negative, aerobic and anaerobic organisms whose growth can be inhibited by the compounds of the invention such as Staphylococcus, Lactobacillus, Streptococcus, Sarcina, Escherichia, Enterobacter, Klebsiella, Pseudomonas, Acinetobacter, Proteus, Citrobacter, Nisseria, Baccillus, Bacteroides, Peptococcus, Clostridium, Salmonella, Shigella, Serratia, Haemophilus, Brucella, and other organisms. In addition to exhibiting highly effective antibacterial activity, the compounds of the invention exhibit increased and improved solubility characteristics as compared with prior quinoline-3-carboxylic acid compounds in the art.

The compounds of Formula I may also be formulated into compositions together with pharmaceutically acceptable carriers for parenteral injections, for oral administration in solid or liquid form, for rectal administration, and the like.

Compositions according to the invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixers containing inert diluents commonly used in the art, such as water. Besides such inert diluents, compositions can also include adjuvants, such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to achieve antibacterial activity in accordance with the desired method of administration. The selected dosage level therefore depends upon the nature of the active compound administered, the route of administration, the desired duration of treatment and other factors. Generally, daily dosage levels of the compounds of Formula I of about 0.1 to about 750, more preferably about 0.25 to about 500 and most preferably about 0.5 to about 300 mg. of active ingredient per kg. of body weight are effective when administered orally to a mammalian patient suffering from an infection caused by a susceptible organisms. If desired, the daily dose may be divided into multiple doses for administration, e.g., two to four times per day.

The compound of Formula I may be prepared in accordance with the following reaction scheme, in which $R_2$ is as described above and X can be independently identical or non-identical halogen.

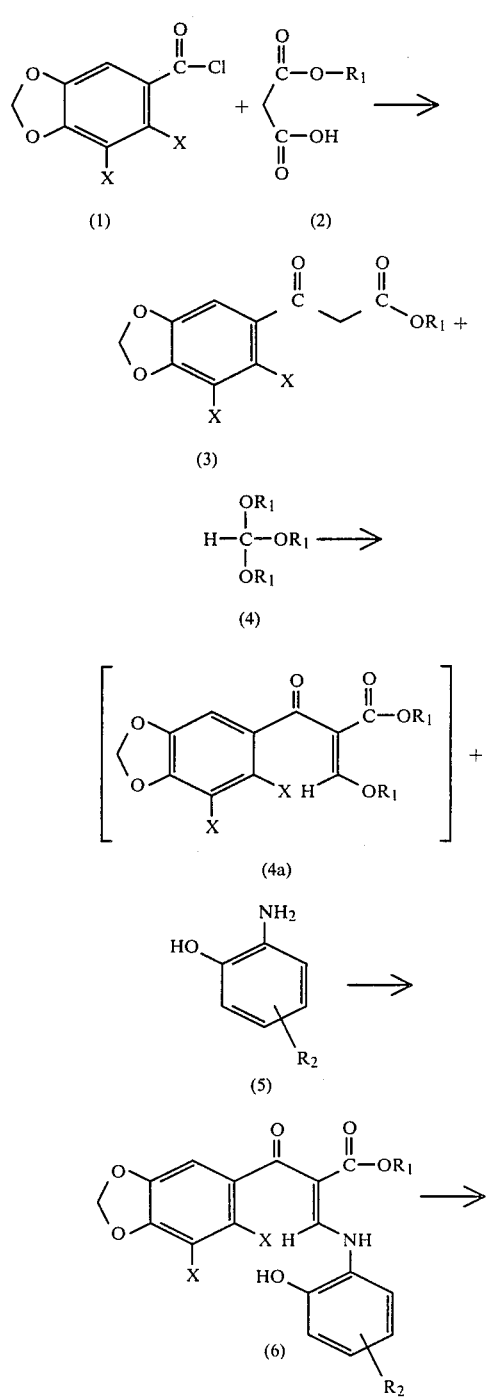

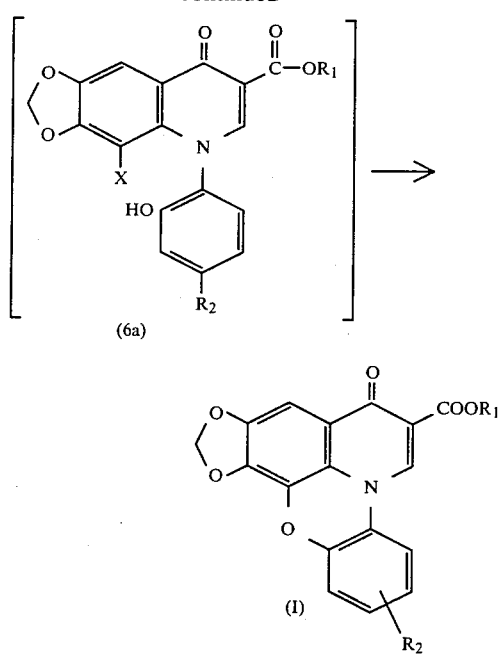

In accordance with the foregoing reaction scheme, 2,3-dibromo-4,5-methylenedioxybenzoyl chloride is reacted with malonic acid halfester (2) in the presence of n-butyllithium to give the β-ketoester (3). The β-ketoester (3) is then treated with a trialkylorthoformate (4) in the presence of an acid anhydride, followed by reaction with substituted or unsubstituted 2-hydroxyaniline (5) to obtain the enaminoketoester (6). This enaminoketoester (6) is then cyclized by treatment with a strong base such as sodium hydride to obtain the 1,2-methylenedioxy-4-oxo-4H-quino[2,3,4-i,j][1,4]benoxazine-5-carboxylic acid ester (I) ($R_1$=alkyl). The ester (I) is subjected to hydrolysis either with hydrochloric acid or sodium hydroxide to form the free acid (I) ($R_1$=H). As used in the following examples, the references to compounds such as (1), (2), (3), etc. and to the substituents, such as R, $R_1$, $R_2$ etc. refer to the corresponding commpounds and substituents in the foregoing reaction scheme and in formula I.

EXAMPLE 1

1,2-methylenedioxy-4-oxo-4H-quino[2,3,4-i,j][1,4]benoxazine-5-carboxylic acid (a) To a dry ice cooled solution of 0.85 g. malonic acid monoethyl ester in 25 ml. of tetrahydrofuran (THF) is slowly added 9.2 ml. of 1.4M n-butyl lithium in THF and the flask is warmed to −5° C. After 5 minutes, the solution is cooled back to −70° C. After 1.3 g. of the acid chloride (1) (X=Br) is added, the cooling bath is removed and warmed up to room temperature over an hour. The solution is then partitioned between 1N HCl and ether. The ether portion is washed with NaHCO3 and is dried over MgSO4, then evaporated to obtain a pale yellow oil which is then purified over a silica gel column to yield β-ketoester (3) ($R_1$=$C_2H_5$, X=Br).

(b) To a solution of 1.25 g. of β-ketoester (3) ($R_1$=$C_2H_5$, X=Br) in 0.8 ml. of triethylorthoformate and 5 ml. of acetic anhydride is heated at 135° C. for 1½ hours with the removal of the ethyl acetate formed during the reaction. The solution is evaporated under reduced pressure to a mobile oil. The oil is then dissolved in 5 ml. of methylene chloride and 0.41 g. of 2-hydroxy-aniline is added into the solution. After 1 hour, the solution is evaporated to dryness and crystallized from ethylacetate yielding (6), wherein $R_1$=$C_2H_5$, X=Br and $R_2$=H.

(c) To a solution of 3.6 g. of the preceding product (6), ($R_1$=$C_2H_5$, $R_2$=H, X=Br) in 30 ml. dimethoxyethane is slowly added 0.56 g. of a 60% sodium hydride-in-oil suspension. The mixture is refluxed for 20 hours and is cooled and diluted with water to a volume of 100 ml. The mixture is then filtered and the solid is washed with a 1:1 hexane/ether solution to obtain (I) ($R_1$=$C_2H_5$, $R_2$=H).

(d) To a suspension of 1.6 g. of (8) ($R_1$=$C_2H_5$, $R_2$=H) in 20 ml. THF is added a sodium hydroxide solution (0.2 g. in 20 ml. water). The mixture is heated at 80° C. for 2 hours resulting in a clear solution which is evaporated under reduced pressure to dryness. The solid is dissolved in 200 ml. water and 1 ml. acetic acid is added. The resulting precipitate is filtered and washed with cold water to produce 1,2-methylenedioxy-4-oxo-4H-quino[2,3,4-i,j][1,4]benoxazine-5-carboxylic acid (I) ($R_1$=H, $R_2$=H).

EXAMPLE 2

1,2-methylenedioxy-10-fluoro-4-oxo-4H-quino[2,3,4-i,j][1,4]benoxazine-5-carboxylic acid The procedure of Example 1 can be repeated replacing 2-hydroxyaniline in 1(b) with 2-hydroxy-4-fluoroaniline to obtain 1,2-methylenedioxy-10-fluoro-4-oxo-4H-quino[2,3,4-i,j][1,4]benoxazine-5-carboxylic acid (I), $R_1$=H, $R_2$=10-fluoro.

EXAMPLE 3

In the described fashion as Example 1, replacing 2-hydroxyaniline in Example 1(b) with appropriate substituted 2-hydroxyaniline, one can obtain the additional substituted 1,2-methylenedioxy-4-oxo-4H-quino[2,3,4-i,j][1,4]benoxazine-5-carboxylic acid (I), ($R_1$=H) as listed in Table I.

TABLE I

| Substituted 2-hydroxyaniline | Compound I obtained ($R_1$ = H) $R_2$ = |
|---|---|
| (a) 6-fluoro | 8-fluoro |
| (b) 5-fluoro | 9-fluoro |
| (c) 3-fluoro | 11-fluoro |
| (d) 4,6-difluoro | 8,10-difluoro |
| (e) 4-chloro | 10-chloro |
| (f) 4-methyl | 10-methyl |
| (g) 4,5-methylenedioxy | 9,10-methylenedioxy |
| (h) 4-hydroxy | 10-hydroxy |
| (i) 4-methoxy | 10-methoxy |

It will be understood that various changes and modifications can be made in the details of formulation, procedure and use without departing from the spirit of the invention, especially as defined in the following claims.

What is claimed is:

1. A compound having the formula:

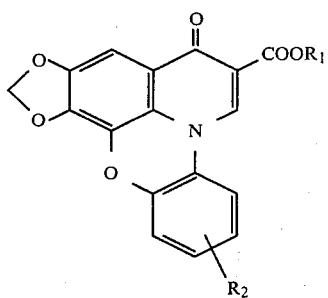

wherein $R_1$ is hydrogen or a carboxy protecting group; $R_2$ is one or more groups selected from the group consisting of hydrogen, halogen, nitro, methylenedioxy, carboxyl, cyano, $C_1$ to $C_6$ alkyl, halo-substituted $C_1$ to $C_6$ alkyl, hydroxy-substituted $C_1$ to $C_6$ alkyl, a group having the formula:

—Y—$R_3$ wherein —Y— is —O— or —S— and $R_3$ is hydrogen or $C_1$ to $C_6$ alkyl, and an amine group having the formula:

wherein $R_4$ and $R_5$ are independently hydrogen or $C_1$ to $C_6$ alkyl; and, pharmaceutically acceptable salts thereof.

2. A compound as defined in claim 1 wherein $R_1$ is hydrogen.

3. A compound as defined in claim 1 wherein $R_2$ is hydrogen and $R_1$ is hydrogen.

4. A compound as defined in claim 1 wherein $R_2$ is loweralkyl and $R_1$ is hydrogen.

5. A compound as defined in claim 1 wherein $R_2$ is 10-fluoro and $R_1$ is hydrogen.

6. A compound as defined in claim 1 wherein $R_2$ is methylenedioxy and $R_1$ is hydrogen.

7. A compound as defined in claim 1 wherein $R_2$ is 8,10-difluoro group, and $R_1$ is hydrogen.

8. A composition having antibacterial activity in pharmaceutical dosage form containing a diluent and a compound as defined in claim 1.

9. A method of treating a bacterial infection in a patient comprising administering to a patient in need of such treatment a therapeutically effective amount of a compound as defined in claim 1.

* * * * *